(12) United States Patent
Graeber et al.

(10) Patent No.: US 9,861,631 B2
(45) Date of Patent: *Jan. 9, 2018

(54) METHODS AND COMPOSITIONS FOR SAFE AND EFFECTIVE TREATMENT OF ERYTHEMA

(71) Applicant: Galderma Laboratories, L.P., Fort Worth, TX (US)

(72) Inventors: Michael Graeber, Lawrenceville, NJ (US); Christian Loesche, Hegenheim (FR); Philip Freidenreich, Yardley, PA (US); Yin-sang Liu, Princeton Junction, NJ (US); Matthew James Leoni, Titusville, NJ (US)

(73) Assignee: Galderma Laboratories, L.P., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/679,598

(22) Filed: Apr. 6, 2015

(65) Prior Publication Data

US 2015/0209350 A1  Jul. 30, 2015

Related U.S. Application Data

(63) Continuation of application No. 14/097,912, filed on Dec. 5, 2013, now abandoned, which is a continuation of application No. 13/637,040, filed as application No. PCT/EP2011/054596 on Mar. 25, 2011, now abandoned.

(60) Provisional application No. 61/282,754, filed on Mar. 26, 2010.

(51) Int. Cl.
| | |
|---|---|
| *A61K 31/194* | (2006.01) |
| *A61K 31/498* | (2006.01) |
| *A61K 9/00* | (2006.01) |
| *A61K 9/06* | (2006.01) |
| *A61K 45/06* | (2006.01) |

(52) U.S. Cl.
CPC .......... *A61K 31/498* (2013.01); *A61K 9/0014* (2013.01); *A61K 9/06* (2013.01); *A61K 31/194* (2013.01); *A61K 45/06* (2013.01)

(58) Field of Classification Search
CPC ...... A61K 31/498; A61K 9/06; A61K 9/0014; A61K 31/194; A61K 45/06
See application file for complete search history.

(56) References Cited

U.S. PATENT DOCUMENTS

| | | |
|---|---|---|
| 3,278,447 A | 10/1966 | McNicholas |
| 3,560,501 A | 2/1971 | Walker |
| 3,594,380 A | 7/1971 | Sulkowski |
| 3,723,432 A | 3/1973 | Ott |
| 3,736,297 A | 5/1973 | Bracke |
| 3,740,442 A | 6/1973 | Ott |
| 3,890,319 A | 6/1975 | Danielewicz et al. |
| 3,968,219 A | 7/1976 | Rahtz et al. |
| 4,011,322 A | 3/1977 | Rahtz et al. |
| 4,029,792 A | 6/1977 | Danielewicz et al. |
| 4,164,570 A | 8/1979 | Clough et al. |
| 4,201,211 A | 5/1980 | Chandrasekaran et al. |
| 4,256,763 A | 3/1981 | McHugh |
| 4,285,967 A | 8/1981 | Gubernick et al. |
| 5,021,416 A | 6/1991 | Gluchowski |
| 5,077,292 A | 12/1991 | Gluchowski |
| 5,112,822 A | 5/1992 | Gluchowski |
| 5,130,441 A | 7/1992 | Gluchowski |
| 5,198,442 A | 3/1993 | Gluchowski |
| 5,204,347 A | 4/1993 | Gluchowski |
| 5,237,072 A | 8/1993 | Gluchowski |
| 5,300,504 A | 4/1994 | Gluchowski |
| 5,326,763 A | 7/1994 | Gluchowski et al. |
| 5,373,010 A | 12/1994 | Gluchowski et al. |
| 5,418,234 A | 5/1995 | Gluchowski et al. |
| 5,424,078 A | 6/1995 | Dziabo et al. |
| 5,442,053 A | 8/1995 | della Valle et al. |
| 5,552,403 A | 9/1996 | Burke et al. |
| 5,561,132 A | 10/1996 | Burke et al. |
| 5,587,376 A | 12/1996 | Burke et al. |
| 5,693,646 A | 12/1997 | Jones et al. |
| 5,696,127 A | 12/1997 | Jones et al. |
| 5,703,077 A | 12/1997 | Burke et al. |
| 5,714,486 A | 2/1998 | Burke et al. |
| 5,720,962 A | 2/1998 | Ivy et al. |
| 5,721,237 A | 2/1998 | Myers et al. |
| 5,736,165 A | 4/1998 | Ripley et al. |

(Continued)

FOREIGN PATENT DOCUMENTS

| | | |
|---|---|---|
| CN | 101380321 A | 3/2009 |
| EP | 0456460 A2 | 11/1991 |

(Continued)

OTHER PUBLICATIONS

Clinical Pharmacology and Biopharmaceutics Reviews (2005).*

(Continued)

*Primary Examiner* — Mina Haghighatian
*Assistant Examiner* — Helen Chui
(74) *Attorney, Agent, or Firm* — Panitch Schwarze Belisario & Nadel LLP

(57) ABSTRACT

Improved methods and compositions for safe and effective treatment of erythema or a symptom associated with erythema in a subject are described. The methods involve topically applying to an affected skin area a topical composition comprising about 0.3% to about 10% by weight of brimonidine and a pharmaceutically acceptable carrier.

8 Claims, 3 Drawing Sheets

(56) References Cited

U.S. PATENT DOCUMENTS

| | | |
|---|---|---|
| 5,753,637 A | 5/1998 | Fried |
| 5,756,503 A | 5/1998 | Burke et al. |
| 5,773,440 A | 6/1998 | Burke et al. |
| 5,888,493 A | 3/1999 | Sawaya |
| 5,910,312 A | 6/1999 | Fried |
| 5,916,574 A | 6/1999 | Fried et al. |
| 5,932,215 A | 8/1999 | de Lacharriere et al. |
| 6,007,846 A | 12/1999 | Klar |
| 6,117,871 A | 9/2000 | Maurer et al. |
| 6,117,877 A | 9/2000 | Fogel |
| 6,194,415 B1 | 2/2001 | Wheeler et al. |
| 6,248,741 B1 | 6/2001 | Wheeler et al. |
| 6,284,765 B1 | 9/2001 | Caffrey |
| 6,294,553 B1 | 9/2001 | Gil et al. |
| 6,294,563 B1 | 9/2001 | Garst |
| 6,323,204 B1 | 11/2001 | Burke et al. |
| 6,387,383 B1 | 5/2002 | Dow et al. |
| 6,432,934 B1 | 8/2002 | Gilbard |
| 6,441,047 B2 | 8/2002 | DeSantis, Jr. |
| 6,444,681 B1 | 9/2002 | Flavahan et al. |
| 6,465,464 B2 | 10/2002 | Wheeler et al. |
| 6,468,989 B1 | 10/2002 | Chang et al. |
| 6,517,847 B2 | 2/2003 | Dow et al. |
| 6,534,048 B1 | 3/2003 | Borgman |
| 6,846,499 B2 | 1/2005 | El Mogy |
| 7,001,615 B1 | 2/2006 | Singh et al. |
| 7,014,858 B2 | 3/2006 | Ashley |
| 7,345,065 B2 | 3/2008 | Gil et al. |
| 7,439,241 B2 | 10/2008 | DeJovin et al. |
| 7,709,533 B2 | 5/2010 | Wang et al. |
| 7,812,049 B2 | 10/2010 | Shanler et al. |
| 7,838,563 B2 | 11/2010 | DeJovin et al. |
| 8,053,427 B1* | 11/2011 | Buge .................... A61K 31/135 424/1.25 |
| 8,163,725 B1 | 4/2012 | Buge et al. |
| 8,231,885 B2 | 7/2012 | DeJovin et al. |
| 8,394,800 B2 | 3/2013 | DeJovin |
| 8,410,102 B2* | 4/2013 | Graeber ................ A61K 9/0014 424/401 |
| 8,426,410 B2 | 4/2013 | DeJovin et al. |
| 8,513,247 B2* | 8/2013 | Graeber ................ A61K 9/0014 514/230.5 |
| 8,513,249 B2* | 8/2013 | Graeber ................ A61K 9/0014 514/230.5 |
| 8,557,817 B2 | 10/2013 | DeJovin et al. |
| 8,586,586 B2 | 11/2013 | Graeber et al. |
| 8,859,551 B2 | 10/2014 | DeJovin et al. |
| 8,911,713 B2 | 12/2014 | Bouvier et al. |
| 8,916,562 B2 | 12/2014 | Graeber et al. |
| 8,993,571 B2 | 3/2015 | DeJovin et al. |
| 9,034,830 B2 | 5/2015 | Nanduri et al. |
| 9,072,739 B2 | 7/2015 | DeJovin |
| 2001/0031273 A1 | 10/2001 | Simonnet |
| 2001/0031754 A1 | 10/2001 | Gil et al. |
| 2002/0032201 A1 | 3/2002 | Olejnik et al. |
| 2002/0197300 A1 | 12/2002 | Schultz et al. |
| 2003/0017199 A1 | 1/2003 | Woodward et al. |
| 2003/0068343 A1 | 4/2003 | Muizzuddin et al. |
| 2003/0077301 A1 | 4/2003 | Maibach et al. |
| 2003/0087962 A1 | 5/2003 | Demopulos et al. |
| 2003/0229088 A1 | 12/2003 | Gil et al. |
| 2004/0092482 A1 | 5/2004 | Gupta |
| 2004/0156873 A1 | 8/2004 | Gupta |
| 2004/0220259 A1 | 11/2004 | Yu et al. |
| 2004/0242588 A1* | 12/2004 | Dejovin et al. ............... 514/249 |
| 2004/0254252 A1 | 12/2004 | Engles et al. |
| 2004/0266776 A1 | 12/2004 | Gil et al. |
| 2005/0020600 A1 | 1/2005 | Scherer |
| 2005/0059664 A1 | 3/2005 | Gil et al. |
| 2005/0059744 A1 | 3/2005 | Donello et al. |
| 2005/0124593 A1 | 6/2005 | Bernstein |
| 2005/0196418 A1 | 9/2005 | Yu et al. |
| 2005/0276830 A1 | 12/2005 | DeJovin et al. |
| 2006/0057081 A1 | 3/2006 | Boxrud |
| 2006/0171974 A1 | 8/2006 | DeJovin et al. |
| 2006/0233860 A1 | 10/2006 | Chang et al. |
| 2006/0264515 A1 | 11/2006 | Dejovin et al. |
| 2006/0294614 A1 | 12/2006 | Pausch |
| 2007/0003622 A1 | 1/2007 | Srinivasan et al. |
| 2007/0082070 A1 | 4/2007 | Stookey et al. |
| 2007/0207222 A1 | 9/2007 | Yu et al. |
| 2007/0258935 A1 | 11/2007 | McEntire et al. |
| 2008/0044497 A1 | 2/2008 | Sussan et al. |
| 2008/0181867 A1 | 7/2008 | Lambert et al. |
| 2008/0293728 A1 | 11/2008 | McIntire et al. |
| 2009/0060852 A1 | 3/2009 | DeJovin et al. |
| 2009/0061020 A1* | 3/2009 | Theobald et al. ............ 424/617 |
| 2009/0130027 A1 | 5/2009 | Shanler et al. |
| 2009/0304826 A1 | 12/2009 | Lane |
| 2010/0028267 A1 | 2/2010 | Horn |
| 2010/0055153 A1 | 3/2010 | Majmudar |
| 2010/0130502 A1 | 5/2010 | DeJovin et al. |
| 2010/0136585 A1 | 6/2010 | Schwind et al. |
| 2010/0227867 A1 | 9/2010 | DeJovin et al. |
| 2011/0104206 A1 | 5/2011 | Nanduri et al. |
| 2011/0118267 A1 | 5/2011 | DeJovin |
| 2011/0286944 A1 | 11/2011 | Graeber et al. |
| 2012/0101104 A1 | 4/2012 | Buge et al. |
| 2012/0214816 A1 | 8/2012 | Graeber et al. |
| 2013/0059857 A1 | 3/2013 | Graeber et al. |
| 2013/0071489 A1 | 3/2013 | Graeber et al. |

FOREIGN PATENT DOCUMENTS

| | | |
|---|---|---|
| EP | 1090630 A1 | 4/2001 |
| EP | 2090307 A1 | 8/2009 |
| EP | 2213335 A2 | 8/2010 |
| GB | 1381979 A | 1/1975 |
| GB | 1589585 A | 5/1981 |
| GB | 1594852 A | 8/1981 |
| JP | H06-16527 A | 1/1994 |
| JP | 2008-500356 A | 1/2008 |
| WO | 8911851 A1 | 12/1989 |
| WO | 9100088 A1 | 1/1991 |
| WO | 9510280 A1 | 4/1995 |
| WO | 9613267 A2 | 5/1996 |
| WO | 9625163 A1 | 8/1996 |
| WO | 9704764 A1 | 2/1997 |
| WO | 9836730 A2 | 8/1998 |
| WO | 0023066 A2 | 4/2000 |
| WO | 0061144 A1 | 10/2000 |
| WO | 0076502 A1 | 12/2000 |
| WO | 0113955 A1 | 3/2001 |
| WO | 03030813 A2 | 4/2003 |
| WO | 2004105703 A2 | 12/2004 |
| WO | 2005002580 A1 | 1/2005 |
| WO | 2005010025 A2 | 2/2005 |
| WO | 2005115395 A2 | 12/2005 |
| WO | 2009032223 A1 | 3/2009 |
| WO | 2009082452 A1 | 7/2009 |
| WO | 2009158646 A1 | 12/2009 |
| WO | 2010136585 A2 | 12/2010 |
| WO | 2011053487 A1 | 5/2011 |

OTHER PUBLICATIONS

Szabo, "Imidazoline antihypertensive drugs: a critical review on their mechanism of action," Pharmacology & Therapeutics, vol. 93, pp. 1-35 (2002).

Balogh et al., "3D QSAR models for alpha2a-adrenoceptor agonists," Neurochemistry International, vol. 51, pp. 268-276 (2007).

Ruffolo et al., "Alpha- and Beta-Adrenoceptors: From the Gene to the Clink. 2. Structure-Activity Relationships and Therapeutic Applications," Journal of Medicinal Chemistry, vol. 38, No. 19, pp. 3681-3716 (1995).

Day et al., "Use of pimecrolimus cream in disorders other than atopic dermatitis," Journal of Cutaneous Medicine and Surgery, vol. 12, No. 1, pp. 17-26 (2008) (abstract only).

Kosari et al., "Case report: Fluocinonide-induced perioral dermatitis in a patient with psoriasis," Dermatology Online Journal, vol. 15, No. 3 (2009).

(56) References Cited

OTHER PUBLICATIONS

Duncan, "Differential inhibition of cutaneous T-cell-mediated reactions and epidermal cell proliferation by cyclosporin A, FK-506, and rapamycin," Journal of Investigative Dermatology, vol. 102, No. 1, pp. 84-88 (1994).
Nichols et al., "Structure-Activity Relationships for alpha-Adrenoceptor Agonists and Antagonists," Alpha-Adrenoceptors: Molecular Biology, Biochemistry and Pharmacology, ed: Robert R. Ruffolo, Jr., pub: Karger, pp. 75-114 (1991).
Pérez-Rivera et al, "Increased Reactivity of Murine Mesenteric Veins to Adrenergy Agonists: Functional Evidence Supporting Increased alpha1-Adrenoceptor Reserve in Veins Compared with Arteries," Journal of Pharmacology and Experimental Therapeutics, vol. 308, No. 1, pp. 350-357 (2004).
Hirafuji et al, "Noradrenaline stimulates 5-hydroxytryptamine release from mouse ileal tissues via alpha(2)-adrenoceptors," European Journal of Pharmacology, vol. 432, No. 2-3, pp. 149-152 (Dec. 7, 2001) (Abstract only).
Prisant, "Transdermal clonidine skin reactions," Journal of Clinical Hypertension, vol. 4, No. 2, pp. 136-138 (Mar.-Apr. 2002) (Abstract only).
Lueg et al, "Transdermal clonidine as an adjunct to sustained-release diltiazem in the treatment of mild-to-moderate hypertension," Clinical Therapeutics, vol. 13, No. 4, pp. 471-481 (Jul.-Aug. 1991) (Abstract only).
Holdiness, "A review of contact dermatitis associated with transdermal therapeutic systems," Contact Dermatitis, vol. 20, No. 1, pp. 3-9 (Jan. 1989) (Abstract only).
Schmidt et al, "Transdermal clonidine compared with hydrochlorothiazide as monotheraphy in elderly hypertensive males," Journal of Clinical Pharmacology, vol. 29, No. 2, pp. 133-139 (Feb. 1989) (Abstract only).
Osborne et al, "The importance of accurate dosage of topical agents: a method of estimating involved area and application to calcipotriol treatment failures," JEADV vol. 16, pp. 367-373 (2002).
U.S. Appl. No. 14/084,172 by Dejovin, filed Nov. 19, 2013.
Material Safety Data Sheet, pp. 1-2 (1997).
Rebora, "The Management of Rosacea", Am. J. Clin. Dermatol., vol. 3, No. 7, pp. 489-496 (2002).
Burke et al, "Preclinical Evaluation of Brimonidine", Survey of Ophthalmology, vol. 41, pp. S9-S18 (1996).
Guarrera et al, "Flushing in Rosacea: A Possible Mechanism", Arch. Dermatol. Res., vol. 272, pp. 311-316 (1982).
Lindgren et al, "Effects of Some Antihypertensive Drugs on Cutaneous Blood Flow and Inflammatory Skin Responses Following Allergen Challenge in Guinea Pigs", Pharmacology and Toxicology, vol. 60, pp. 364-367 (1987).
Nielsen et al, "Postjunctional a2-adrenoceptors mediate vasoconstriction in human subcutaneous resistance vessels", Br. J. Pharmacol., vol. 97, pp. 829-834 (1989).
Int'l Search Report dated Jun. 9, 2011 in Int'l Application No. PCT/EP2011/054597.
Ramey et al, "Rhinitis Medicamentosa", J Investig Allergol Clin Immunol, vol. 16, No. 3, pp. 148-155 (2006).
McGhie, "Brinnonidine: An alpha-2 adrenergic agonist for glaucoma", Journal of the Pharmacy Society of Wisconsin, May/Jun. 2001, pp. 32-36.
Arndt et al, "Manual of Dermatologic Therapeutics", 7th Ed., pp. 176-177 (2007).
Cunliffe et al, Br. Med. J. 105 (1977).
Shanler et al, "Arch Dermatol", vol. 143, No. 11, pp. 1369-1371 (2007).
Wilkin et al, J. Am. Acad. Dermatol., vol. 46, pp. 584-587 (2002).
Webster, "Rosacea and related disorders", Dermatology, vol. 1, Chapter 39, pp. 545-552 (2003).
Wymenga et al, "Management of Hot Flushes in Breast Cancer Patients", Acta Ocologica, vol. 41, No. 3, pp. 269-275 (2002).
Scruggs, "The Teardrop Sign: a Rare Dermatological Reaction to Brimonidine", Br. J. Opthalmol., vol. 84, pp. 671-672 (2000).

Sakakibara et al, "Treatment of Primary Erythromelalgia with Cyproheptadine", Journal of the Autonomic Nervous System, vol. 58, Nos. 1-2, pp. 121-122 (1996).
Jeyara et al, "Cooling Evokes Redistribution of a2C-Andrenoceptors from Golgi to Plasma Membrane in Transfected Human Embryonic Kidney 293 Cells", Molecular Pharmacology, vol. 60, No. 6, pp. 1195-1200 (2001).
Fuchs et al, "Heat, but not Mechanical Hyperalgesia, following Andrenergic Injections in Normal Human Skin", Pain, vol. 90, Nos. 1-2, pp. 15-23 (2001).
Morrison et al, "Andrenergic Modulation of a Spinal Sympathetic Reflex in the Rat", J. Pharmacol. Experim. Therap., vol. 273, No. 1, pp. 380-385 (1995).
Yaksh et al, "Reversal of Nerve Ligation-Induced Allodynia by Spinal Alpha-2 Andrenoceptor Agonists", J. Pharmacol. Experim. Therap., vol. 272, No. 1, pp. 207-214 (1995).
Waldron et al, "Relative Contribution of Different Vascular Beds to the Pressor Effects of a-Adrenoceptor Agonists and Vasopressin in Pithed Rats: Radioactive Microsphere Determination", J. Auton. Pharmac., vol. 5, pp. 333-338 (1985).
Bockman et al, "Binding and Functional Characterization of Alpha-2 Andrenergic Receptor Subtypes on Pig Vascular Endothelium", J. Pharmacol. Exp. Therapeutics, vol. 267, pp. 1126-1133 (1993).
Chein et al, "Corneal and conjunctival/scleral penetration of p-aminoclonidine, AGN 190342 and clonidine in rabbit eyes", Current Eye Research, vol. 9, No. 11 pp. 1051-1059 (1990).
Chotani et al, "Silent asc-adrenergic receptors enable cold-induced vasoconstriction in cutaneous arteries", Am. J. Physiol. Heart Circ. Physiol., vol. 278, pp. H1075-H1083 (2000).
Freedman et al, "Estrogen raises the sweating threshold in postmenopausal women with hot flashes", Fertility and Sterility, vol. 77, No. 3, pp. 487-490 (2002).
Nakamura et al, "Peripheral analgesic action of clonidine: mediation by release of endogenous enkephlin-like substances", European Journal of Pharmacology, vol. 146, pp. 223-228 (1988).
Walters, "Development and Use of Brimonidine in Treating Acute and Chronic Elevations of Intraocular Pressure: A Review of Safety, Efficacy, Dose Response, and Dosing Studies", Survey of Ophthalmology, vol. 41, pp. S19-S26 (1996).
Wilkin, "Effect of Subdepressor Clonidine on Flushing Reactions in Rosacea", Arch. Dermatol., vol. 119, pp. 211-214 (1983).
Wilkin, "Why is flushing limited to a mostly facial cutaneous distribution?", J. Am. Acad. Dermatol., vol. 19, pp. 309-313 (1988).
Gennaro, "Remington: The Science and Practice of Pharmacy", 19th Ed., pp. 866-885, 1517-1518, 1577-1597, 1672-1673 (1995).
Berge et al, "Pharmaceutical Salts", Journal of Pharmaceutical Sciences, vol. 66, No. 1, pp. 1-19 (1977).
Int'l Search Report dated Mar. 29, 2011 in Int'l Application No. PCT/US2010/057184; Written Opinion.
Search Report dated Jun. 1, 2011 in FR Application No. 1058612; Written Opinion.
Giordano et al, "Physical Properties of Parabens and Their Mixtures: Solubility in Water, Thermal Behavior, and Crystal Structures," Journal of Pharmaceutical Sciences, vol. 88, No. 11, pp. 1210-1216 (1999).
Perlovich et al, "Thermodynamics of solubility, sublimation and solvation processes of parabens," European Journal of Pharmaceutical Sciences, vol. 24, pp. 25-33 (2005).
Int'l Search Report dated Jun. 9, 2011 in Int'l Application No. PCT/EP2011/054596; Written Opinion.
Center for Drug Evaluation and Research, Clinical Pharmacology and Biopharmaceutics Review(s), Application No. 21-764 (Feb. 4, 2005).
U.S. Appl. No. 13/791,059 by Graeber, filed Mar. 8, 2013.
U.S. Appl. No. 14/097,912 by Graeber, filed Dec. 5, 2013.
Culp et al., "Rosacea: A Review," Pharmacy & Therapeutics, vol. 34, No. 1, pp. 38-45 (2009).
Roberson et al., "Psoriasis genetics: breaking the barrier," Trends in Genetics, vol. 26, No. 9, pp. 415-423 (2010).
Kurian et al., "Current Effective Topical Therapies in the Management of Psoriasis," Skin Therapy Letter, vol. 16, No. 1, pp. 4-7 (2011).

(56) References Cited

OTHER PUBLICATIONS

Schön et al., "Psoriasis", The New England Journal of Medicine, vol. 352, No. 18, pp. 1899-1912 (2005).
Korting et al., "Liposome encapsulation improves efficacy of betamethasone dipropionate in atopic eczema but not in psoriasis vulgaris," European Journal of Clinical Pharmacology, vol. 39, pp. 349-351 (1990).
Khandpur et al., "Topical immunomodulators in dermatology," Journal of Postgraduate Medicine, vol. 50, No. 2, pp. 131-139 (2004).
Ruffolo et al., "Receptor Interactions of Imidazolines: alpha-Adrenoceptors of Rat and Rabbit Aortae Differentiated by Relative Potencies, Affinities and Efficacies of Imidazoline Agonists," British Journal of Pharmacology, vol. 77, pp. 169-176 (1982).
Waugh et al., "Phe-308 and Phe-312 in Transmembrane Domain 7 Are Major Sites of alpha1-Adrenergic Receptor Antagonist Binding," The Journal of Biological Chemistry, vol. 276, No. 27, pp. 25366-25371 (2001).
Pigini et al., "Structure-Activity Relationship at alpha-Adrenergic Receptors Within a Series of Imidazoline Analogues of Cirazoline," Bioorganic & Medicinal Chemistry, vol. 8, pp. 883-888 (2000).
Hieble et al., "Alpha- and Beta-Adrenoceptors: From the Gene to the Clininc. 1. Molecular Biology and Adrenoceptor Subclassification," Journal of Medicinal Chemistry, vol. 38, No. 18, pp. 3415-3444 (1995).
Blount et al., "Rosacea: A Common, Yet Commonly Overlooked, Condition," American Family Physician, vol. 66, No. 3 (2002).
Borbujo et al., "Postjunctional Alpha-1 and Alpha-2 Adrenoceptors in Human Skin Arteries. An in Vitro Study," Journal of Pharmacology and Experimental Therapeutics, vol. 249, No. 1 (1989).
Flavahan, "The Role of Vascular a2-Adrenoceptors as Cutaneous Thermosensors," News in Physiological Sciences, vol. 6 (1991).
Jasper et al., "Ligand Efficacy and Potency at Recombinant a2 Adrenergic Receptors," Biochemical Pharmacology, vol. 55, pp. 1035-1043 (1998).
Lewis et al., "Topical Therapies for Glaucoma: What Family Physicians Need to Know," Am. Fam. Physician, vol. 59, No. 7, pp. 1871-1879 (1999).
Spada et al., "Differential Effects of a-Adrenoceptor Agonists on Human Retinal Microvessel Diameter," Journal of Ocular Pharmacology and Therapeutics, vol. 17, No. 3, pp. 225-277 (2001).
"Dorland's Illustrated Medical Dictionary," W.B. Saunders Company, Ed. 28, pp. 576-577 (1994).
Bohn et al., "Draft Clinical Study Report: A Phase I, Single-Center, Two-Way Crossover Relative Bioavailability Study of Col-118 Administered Topically as a 0.2% Facial Gel and Brimonidine Opthalmic Solution 0.2$ Administered to the Eye in Normal Healthy Male and Female Volunteers," CollaGenex Pharmaceuticals, Inc., Clinical Study Report No. 7432-106, pp. 1-5, Draft 1: Oct 29, 2007.
Wyatt et al., "Dermatological Pharmacology," Goodman & Gilman's The Pharmacological Basis of Therapeutics, McGraw-Hill., Ed. 10, pp. 1795-1848 (2001).
Koleng et al., "Carbomer," Handbook of Pharmaceutical Excipients, American Pharmaceutical Association, Ed. 3, pp. 79-82 (2000).
Walsh et al., "Physicians' Desk Reference," Medical Economics Company, Inc., Ed. 56, pp. 54-56 (2002).
Remington, "The Science and Pharmacy," Mack Publishing Company, pp. 1517-1518, 1577-1591 (1995).
Prosecution History of U.S. Appl. No. 10/626,037, filed Jul. 23, 2003 by Sherer.
FOI Services, Inc., "Alphagan 0.5% Opthalmic Solution (Allergan) Mar. 13, 1997 Approval: Approval Letter; Not-Approvable Letter," (1997).
Adkins et al., "Brimonidine: A Review of its Pharmacological Properties and Clinical Potential in the Management of Open-Angle Glaucoma and Ocular Hypertension," Drugs and Aging, vol. 12, No. 3, pp. 225-241 (1998).
Barry, "Dermatological Formulations," Marcel Dekker, Inc., pp. 1-126 (1983).
FOI Services, Inc., "Alphagan 0.5% Ophthalmic Solution (Allergan) Mar. 13, 1997 Approval: Clinical Pharmacology & Biopharmaceutics," (1997).
Hornqvist et al., "Adrenoceptor-mediated responses in human skin studied by iontophoresis," British Journal of Dermatology, vol. 3, pp. 561-566 (1984).
Bashaw, "Clinical Pharmacology/Biopharmaceutics Review," Department of Health & Human Services, Application No. 21-770 (2005).
Decauchy et al., "Rosacea," Rev. Prat (Paris), vol. 43, No. 18, pp. 2344-2348 (1993).
Zhang et al, "Clinical Pharmacology/Biopharmaceutics Review(s)," Department of Health & Human Services, Application No. 21-764 (2005).
Acheampong et al., "Measurement of brimodine concentrations in human plasma by a highly sensitive gas chromatography/mass spectrometric assay," Journal of Pharmaceutical and Biomedical Analysis, vol. 13, pp. 995-1002 (1995).
Acheampong et al., "Effect of Ocular Dose on the Systemic Absorption and Disposition of Brimonidine in Humans," Pharmaceutical Research, Official Journal of the American Association of Pharmaceutical Scientists, Plenum Press, vol. 2, No. 10 (1994).
Tandon, "Review and Evaluation of Pharmacology/Toxicology Data," Ceneter for Drug Evaluation and Research, Application No. 21-262 (2000).
Bill et al., "Ocular Effects of Clonidine in Cats and Monkeys," Exp. Eye Res., vol. 21, pp. 481-488 (1975).
Cross et al., "Transdermal Penetration of Vasoconstrictors—Present Understanding and Assessment of the Human Epidermal Flux and Retention of Free Bases and Ion-Pairs," Pharmaceutical Research, vol. 20, No. 2 (2003).
Grosshans, "Rosacea," La Press Medicale, vol. 17, No. 45, pp. 2393-2398 (1988).
Grosshans et al., "Rilménidine dans la Rosacée: Étude en Double insu contra placebo," Ann. Dermatol. Venereol., vol. 124, pp. 687-691 (1997).
Langer et al., "Recent Developments in Noradrenergic Neurotransmission and its Relevance to the Mechanism of Action of Certain Antihypertensive Agents," Hypertension, vol. 2, pp. 372-382 (1980).
Ma et al., "The Efficacy of 0.2% Brimonidine for Preventing Intraocular Pressure Rise Following Argon Laser Trabeculoplasty," Korean Journal of Ophthalmology, vol. 13, pp. 78-84 (1999).
Robin, "Short-term Effects of Unilateral 1% Apraclonidine Therapy," Arch Ophthalmol., vol. 106, pp. 912-915 (1988).
Sibenge et al., "Rosacea: A study of clinical patterns, blood flow, and the role of Demodex folliculorum," J. Am. Acad. Dermatol., vol. 26, pp. 590-593 (1992).
Uva et al., "Cutaneous Manifestations of Systemic Lupus Erythematosus," Autoimmune Diseases, vol. 2012, pp. 1-15 (2012).
Van Landuyt et al., "Traitment de la Rosacée," Ann. Dermatol. Venereol., vol. 124, pp. 729 (1997).
Zuber, "Rosacea: Beyond First Blush," Hospital Practice, vol. 32, No. 2, pp. 188-189 (1997).
Defendant's Initial Validity Contentions issued Jan. 13, 2016 in U.S. District Court for the District of Delaware for *Galderma Laboratories, L.P., and Nestlé Skin Health S.A.* v. *Actavis Laboratories UT, Inc.*
"Ocular Rosacea Fact Sheet", pp. 1-3 (Feb. 1, 2001).
Eye Pain and Light Sensitivity, Richmond Eye Associates. Feb. 1, 2001, downloaded from web page: http://www.richmondeye.com/eyehealth_pain/, Download date: Jun. 25, 2016, original posting date Sep. 23, 2015, 3 pages.
Flavahan, "Are Human Vascular a-Adrenoceptors Atypical?", Journ. of Cardio Pharm., vol. 6, pp. 208-210 (1984).
Flavahan et al., "Cooling and a-1 and a2-adrenergic Responses in Cutaneous Veins: Role of Receptor Reserve", AM J Physiol Heart, vol. 249, pp. H950-H955 (1985).
Flavahan et al., "Denervation Augments Alpha-2 but Not Alpha-1 Adrenergic Responses in Canine Saphenous Veins", Journ. of Pharm., vol. 240, No. 2, pp. 589-593 (1987).

(56) References Cited

OTHER PUBLICATIONS

Nielsen et al., "Differential Distribution of Postjunctional a2 Adrenoceptors in Human Omental Small Arteries", Journ. of Cardio Pharm., vol. 16, pp. 34-40 (1990).
Flavahan et al., "Effect of Cooling on Alpha-1 and Alpha-2 Adrenergic Responses in Canine Saphenous and Femoral Veins", Journ. of Pharm., vol. 238, No. 1, pp. 139-147 (1986).
Komori, et al., "Electrophysiological Analysis of Adrenergic Neurotranmission and It's Modulation by Chronic Denervation in Canine Saphenous Veins", Journ. of Pharm., vol. 252, No. 3, pp. 1197-1201 (1989).
Freedman et al., "Gender Differences in Modulation of Peripheral Vascular Adrenoceptors", Society of Behav. Medicine, vol. 17, No. 1, pp. 15-18 (1995).
Tornebrandt et al., "Pharmacological Characterization of Alpha-Adrenergic Receptor Subtypes Mediating Contraction in Human Mesenteric Arteries and Veins", Blood Vessels, vol. 22, pp. 179-195 (1985).
Steen, et al., "Pharmacological Characterization of Postjuntional a-adrenoceptors in Isolated Human Omental Arteries and Veins", Acta Physiol Scand., vol. 120, pp. 109-116 (1984).
Sjoberg et al., "Postjunctional a-Adrenoceptors in Human Superficial Epigastric Arteries and Veins", Pharm &Toxic., vol. 60, pp. 43-50 (1987).
Nase et al., "Postjunctional a2-adrenoceptors are Not Present in Proximal Arterioles of Rat Intestine", Amer. Physio. Society, vol. 274, pp. H202-H208 (1998).
Steen et al., "Postjunctional a1- and a2-adrenoceptors Mediating Contraction in Isolated Human Groin Arteries and Veins", Acta Physiol Scand., vol. 122, pp. 323-329 (1984).
Wigley et al., "Raynaud's Phenomenon", Rheuma. Disease Clin., vol. 22, No. 4, pp. 765-781.
Stevens et al., "Heterogeneity of Post-Junctional a-Adrenoceptors in Human Vascular Smooth Musle", Arch. Intl. Pharma., vol. 254, pp. 43-57 (1981).
Bini et al., "Thermoregulatory and Rhythm-Generating Mechanisms Governing the Sudomotor and Vasconstrictor Outflow in Human Cutaneous Nerves", J. Physiol., vol. 306, pp. 537-552 (1980).
Bini et al., "Regional Similarities and Differences in Thermoregulatory Vaso- and Sudomotor Tone", J. Physiol., vol. 306, pp. 553-565 (1991).
Blochl-Daum et al., "In Vivo Studies on Alpha-Adrenergic Receptor Subtypes in Human Veins", Naunyn-Schmied. Arch Pharma., vol. 344, pp. 302-307 (1991).
Brinnel et al., "Rosacea: Disturbed Defense Against Brain Overheating", Arch Dermatol. Res., vol. 281, pp. 66-72 (1989).
Clayden et al., "Menopausal Flushing: Double-Blind Trial of a Non-Hormonal Medication", Brit. Med. Journ., vol. 1, pp. 409-412 (1974).
Coffman et al., "Role of Alpha-Adrenoceptor Subtypes Mediating Sympathetic Vasoconstriction in Human Digits", Euro. Journ. Clinical Invest., vol. 18, pp. 309-313 (1988).
Coffman et al., "a-2-Adrenergic and 5-HT2 Receptor Hypersensitivity in Raynaud's Phenomenon" Joum of Vascular Med and Biol., vol. 2, No. 3, pp. 100-106 (1990).
Cunliffe et al., "Rosacea, Migraine, Dixarit", Summaries of Papers, pp. 11-12 (1974).
Drew et al., "Evidence for Two Distinct Types of Postsynaptic a-Adrenoceptor in Vascular Smooth Muscle in vivo", Br. J. Pharmac., vol. 67, pp. 207-215 (1979).
Edington et al., "Clonidine (Dixarit) for Menopausal Flushing", CMA Journal, vol. 123, pp. 23-26 (1980).
Ekenvall et al., "a-Adrenoceptors and Cold-Induced Vasoconstriction in HUman Finger Skin", American Physio. Society, pp. H1000-H1003 (1988).
Faber, "In Situ Analysis of a-Adrenoceptors on Arteriolar and Venular Smooth Muscle in Rat Skeletal Muscle Microcirculation", Circulation Research, vol. 62, No. 1, pp. 37-50 (1988).
Flavahan et al., "Blockade by Yohimbine of Prazosin-Resistant Pressor Effects of Adrenaline in the Pithed Rat", Br. J. Pharmac., vol. 69, pp. 355-357 (1980).
Flavahan et al., "Characterization of Postjunctional Alpha-1 and Alpha-2 Adrenoceptors Activated by Exogenous or Nerve-Released Norepinephrine in the Canine Saphenous Vein", The Journ. Pharm., vol. 230, No. 3 (1984).
Flavahan et al., "Human Postjuntional Alpha-1 and Alpha-2 Adrenoceptors: Differential Distribution in Arteries of the Limbs", The Journ. of Pharm., vol. 241, No. 2, pp. 361-365 (1987).
Flavahan et al., "Increased a-2-Adrenergic Constriction of Isolated Arterioles in Diffues Scleroderma", Amer. College of Rheum., vol. 43, No. 8, pp. 1886-1890 (2000).
Flavahan, "Thermoregulation: The Normal Structure and Function of the Cutaneous Vascular System", John Hopkins Univ., pp. 37-55 (2014).
Freedman et al., "Local Temperature Modulates a1- and a2-adrenergic Vasoconstriction in Men", Dept. of Psychiatry, pp. H1197-H1200 (1992).
Freedman, "Physiology of Hot Flashes", Amer. Journ. of Human Biol., vol. 13, pp. 453-464 (2001).
Haefeli et al., "Lack of Role of Endothelium-Derived Relaxing Factor in Effects of a-adrenergic Agonists in Cutaneous Veins in Humans", Div. of Clinical Pharmol., pp. H364-H369 (1993).
Kakizoe et al., "Spectrophotometric Study of a-Adrenoceptors Affecting Microcirculation of Rat Skin", Clin. Experi. Pharmo., vol. 20, pp. 421-427 (1993).
Kellogg et al., "Cutaneous Active Vasodilation in Humans is Mediated by Cholinergic Nerve Cotransmission", Circres. AHA Journals, vol. 77, pp. 1222-1228 (1995).
Kooner et al., "Hemodynamic and Neurohormonal Effects of Clonidine in Patients with Preganglionic and Postganglionic Sympathetic Lesions Evidence for a Central Sympatholytic Action", Circulation, vol. 84, No. 1, pp. 75-83 (1991).
Koos, "Characterization of Adrenoceptor Subtypes in Cat Cutaneous Vasculature", Journ. of Pharma, vol. 254, No, 1, pp. 221-227 (1990).
Lindblad et al., "Alpha-adrenoceptors in the Vessels of Human Finger Skin", Acta Physiol Scand., vol. 128, pp. 219-222 (1986).
Lindblad et al., "Adrenoceptors in Raynaud's Disease", Journ. of Cardio Pharma., vol. 14, pp. 881-885 (1989).
Minson et al., "Nitric Oxide and Neurally Mediated Regulation of Skin Blood Flow During Local Heating", J. Appl. Physiol., vol. 91, pp. 1619-1626 (2001).
Nagamani et al., "Treatment of Menopausal Hot Flashes with Transdermal Administration of Clonidine", Am J. Obstet Gynecol., vol. 156, pp. 561-565 (1987).
Nagasaka et al., "Selective Brain Cooling in Hyperthermia: The Mechanisms and Medical Implications", Med. Hypoth., vol. 50, pp. 203-211 (1998).
Ruffolo et al., "Pharmacologic and Therapeutic Applications of a2-Adrenoceptor Subtypes", Annu. Rev. Toxicol., vol. 32, pp. 243-278 (1993).
Saunders et al, "Localization and Trafficking of a2-adrenergic Receptor Subtypes in Cells and Tissues", Pharma. & Thera., vol. 84, pp. 193-205 (1999).
Shaw, et al., "The Perimenopausal Hot Flash: Epidemiology Physiology, and Treatment", Nurse Practitioner, vol. 22, No. 3, pp. 55-66 (1997).
Stephens et al., "The Influence of Topical Capsaicin on the Local Thermal Control of Skin Blood Flow in Humans", Am. J. Physiol Reg., vol. 281 ,pp. R894-R901 (2001).
Wilkin et al., "Oral Thermal-Induced Flushing in Erythematotelangiectatic Rosacea", Journ. of Invest. Derma., vol. 76, No. 1, pp. 15-18 (1981).
Wilkin, "Reconizing and Managing Rosacea", Drug Therapy, pp. 41-49 (1993).
Ruffolo, "a-Adrenoceptors: Molecular Biology, Biochemistry and Pharmacology", Progress in Basic and Clinical Pharmacology, vol. 8, 239 pgs (1991).
Shepherd et al., "The Human Cardiovascular System", Facts and Concepts, Raven Press, 359 pgs.(1979).

(56) References Cited

OTHER PUBLICATIONS

Kibbe, "Carbomer", Handbook of Pharaceutical Excipients, American Pharm Assoc., Third Edition, 6 pgs. (2000).
FOI Services, Inc., "Alphagan 0.5% Opthalmic Solution (Allergan) Sep. 6, 1996 Approval: Approval Letter; Not-Approvable Letter," (1996).
"Guidance for Industry: Statistical Approaches to Establishing Bioequivalebce" US Dept. of Health and Human Services, 48 pgs (2001).
"Guideline for Industry: Dose-Response Information to Support Drug Registration", Federal Register, vol. 59, No. 216, 17 pgs. (1994).
Stahl et al. "Handbook of Pharmaceutical Salts Properties, Selection, and Use", International of Pure and Applied Chemistry, 5 pgs (2002).
Cantor, "The Evolving Pharmacotherapeutic Profile of Brimonidine, an a2-adrenergic Agonist, After Four Years of Continuous Use", Exp. Opin. Pharmacother, vol. 1, No. 4, pp. 815-834 (2000).
Wilkins, "Rosacea", Arch Dermatol., vol. 130, pp. 359-362 (1994).
Dermatitis Medicamentose: Severe Rebound Erythem Secondary to Topical Brimonidine in Rosacea, Dermatology Online Journal, Mar. 2015, downloaded from web page: http://escholarship.org/uc/item/93n0n7pp, Download date: Nov. 15, 2016, original posting date: 2015, 5 pages.
Fowler et al., "Efficacy and Safety of Once-Daily Topical Brimonidine Tartrate Gel 0.5% for the Treatment of Moderate to Severe Facial Erythema of Rosacea: Results of Two Randomized, Double-Blind, Vehicle-Controlled Pivotal Studies", Journ. of Drugs Derma., vol. 12, No. 6, pp. 650-656 (2013).
Nielsen, "A Double-Blind Study of 1% Metronidazole Cream Versus Systemic Oxytetracycline Therapy", Brit. Journ. of Derma., vol. 109, pp. 63-65 (1983).
Fowler et al., "Once-Daily Topical Brimonidine Tartrate Gel 0.5 is a Novel Treatment for Moderate to Severe Facial Erythema of ROsacea:Results of Two Multicentre, Randomized and Vehicle-Controlled Studies", Brit. Journ. of Dermatology, vol. 166, pp. 633-641 (2012).
Tanghetti, et al., "Optimizing the Use of Topical Brimonidine in Rosacea Management: Panel Recommendations", Journ. of Drugs Derma., vol. 14, No. 1, pp. 33-40 (2015).
Van Zuuren et al., "Interventions for Rosacea: Abridges Updated Cochrane Systematic Review Including GRADE Assessments", Brit. Journ. of Derm., vol. 173, pp. 651-662 (2015).
Ilkovitch et al., "Trigeminal Trophic Syndrome Secondary to Recurrent Meningioma", Journ. Am Dermatol., 2 pgs. (2014).
Routt, Rebound Erythema and Burning Sensation from a New Topical Brimonidine Tartrate Gel 0.33%.

* cited by examiner

METHODS AND COMPOSITIONS FOR SAFE AND EFFECTIVE TREATMENT OF ERYTHEMA

CROSS-REFERENCE TO RELATED APPLICATION

This application is a continuation of U.S. patent application Ser. No. 14/097,912, filed Dec. 5, 2013, which is a continuation of U.S. patent application Ser. No. 13/637,040, filed Sep. 25, 2012, which is a Section 371 of International Application No. PCT/EP2011/054596, filed Mar. 25, 2011, which was published in the English language on Sep. 29, 2011, under International Publication No. WO 2011/117377 A2, which is entitled to priority pursuant to 35 U.S.C. §119(e) to U.S. Provisional Patent Application No. 61/282,754, filed Mar. 26, 2010, and the disclosure of which is incorporated herein by reference.

BACKGROUND OF THE INVENTION

Erythema is a skin condition characterized by redness of the skin. It occurs with any skin injury, infection, or inflammation. It can also occur as a reaction to medications, illness or emotions. It can further occur for reasons currently unknown. Erythema is difficult to treat. Currently available treatments for erythema mainly treat the underlying diseases and avoid known triggers. These treatments are of limited effectiveness, particularly for erythema with unknown causes.

Brimonidine, a selective α2-adrenergic agonist, has been used as either a monotherapy or an adjunctive therapy to lower intraocular pressure (IOP) in the treatment of glaucoma and ocular hypertension (OHT) since its approval in 1996. The most common side effects associated with brimonidine therapy are dry mouth, fatigue/drowsiness, headache, mild hyperemia, blurred vision and foreign body sensation. Hypertension, palpitations and syncope have been reported by less than 3% patients in clinical trials involving brimonidine ophthalmic treatment. See McGhie, *Journal of the Pharmacy Society of Wisconsin*, May/June 2001, at World Wide Web: pswi.org/professional/pharmaco/brimonidine.pdf, and references therein. Results from the dose-ranging study in patients with glaucoma or ocular hypertension showed that although 0.5% (w/w) had higher efficacy in the early phase of treatment, the 0.5% (w/w) and 0.2% (w/w) had similar efficacy after two weeks of treatment, and that 0.5% (w/w) had more systemic and ocular side effects than 0.2% (w/w). See, e.g., Walters, *Survey of Ophthalmology*, 1996, 41: S19-S26). Ophthalmic formulations containing 0.2% (w/w) brimonidine have been used for chronic applications to treat glaucoma and ocular hypertension, while that containing 0.5% (w/w) brimonidine has been only used for acute therapy for the prevention of postoperative intraocular pressure spikes. In order to reduce a variety of ocular and systemic side-effects associated with the ophthalmic application of 0.2% (w/w) brimonidine, ophthalmic formulations containing lower concentrations of brimonidine, e.g., 0.15% (w/w) or 0.1% (w/w), have been subsequently developed and used for chronic ophthalmic applications.

Brimonidine has been reported to be useful in treating erythema caused by rosacea. See, e.g., U.S. Ser. No. 10/853,585 to DeJovin et al. To ensure the safety and avoid unacceptable side effects, a previous clinical study used 0.2% (w/w) brimonidine tartrate as the "high" dosage for treating erythema. See US 2009/0061020 to Theobald et al.

In the present invention, it has been surprisingly discovered that topical administration of brimonidine to a skin area affected by erythema or a related symptom resulted in significantly less systemic exposure to brimonidine than topical ophthalmic application of brimonidine. It has been found that although systemic exposure increased with the applied dose of brimonidine, statistical analysis showed that the increase in systemic exposure ($C_{max}$) was not dose proportional, e.g., the increase in the mean $C_{max}$ was much less than the increase in the dose. It has also been discovered that, unlike the topical ophthalmic application of brimonidine, topical administration of higher than 0.2% (w/w) brimonidine to a skin area affected by erythema or a related symptom resulted in increased efficacy without observable loss of effectiveness over time. No unacceptable drug related adverse events was observed with the treatment of higher concentration of brimonidine tested.

Accordingly, a higher concentration of brimonidine, such as about 0.3% (w/w) to about 10% (w/w), can now be used in improved methods and compositions for safe and effective treatment of erythema or a symptom associated therewith.

BRIEF SUMMARY OF THE INVENTION

In one general aspect, embodiments of the present invention relate to a method of providing a safe and effective treatment of erythema or a symptom associated therewith in a subject. The method comprises topically administering to a skin area affected by the erythema or the symptom a topical composition, which comprises about 0.3% to about 10% by weight brimonidine and a pharmaceutically acceptable carrier, wherein the topical administration effects a serum or plasma profile of brimonidine having a mean $C_{max}$ of about 54±28 pg/mL or less and a mean $AUC_{0-24hr}$ of about 568±277 pg·hr/mL or less.

In another general aspect, embodiments of the present invention relate to a method of producing a packaged product for providing a safe and effective treatment of erythema or a symptom associated therewith in a subject. The method comprises:

(1) obtaining a topical composition comprising about 0.3% to about 10% by weight brimonidine and a pharmaceutically acceptable carrier;

(2) devising instructions for topically administering the topical composition to a skin area affected by the erythema or the symptom to obtain the safe and effective treatment, and (3) providing the topical composition and the instructions in a unified package, wherein the topical administration effects a serum or plasma profile of brimonidine having a mean $C_{max}$ of about 54±28 pg/mL or less and a mean $AUC_{0-24hr}$ of about 568±277 pg·hr/mL or less.

In another general aspect, embodiments of the present invention relate to a topical gel composition for providing a safe and effective treatment of erythema or a symptom associated therewith in a subject. The topical gel composition comprises:

about 0.3% (w/w) to about 10.0% (w/w) brimonidine;
about 0.20% (w/w) to about 4.0% (w/w) gelling agent; and
about 5.0% (w/w) to about 30.0% (w/w) at least one polyol, wherein topical administration of the topical gel composition to a skin area affected by the erythema or the symptom effects a serum or plasma profile of brimonidine having a mean $C_{max}$ of about 54±28 pg/mL or less and a mean $AUC_{0-24hr}$ of about 568±277 pg·hr/mL or less.

In a preferred embodiment, the topical composition used in or encompassed by embodiments of the present invention comprises about 0.4% (w/w) to about 0.6% (w/w) brimonidine tartrate.

In another preferred embodiment, the erythema is erythema of rosacea.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

In the drawings.

DETAILED DESCRIPTION OF THE INVENTION

Figure 1:
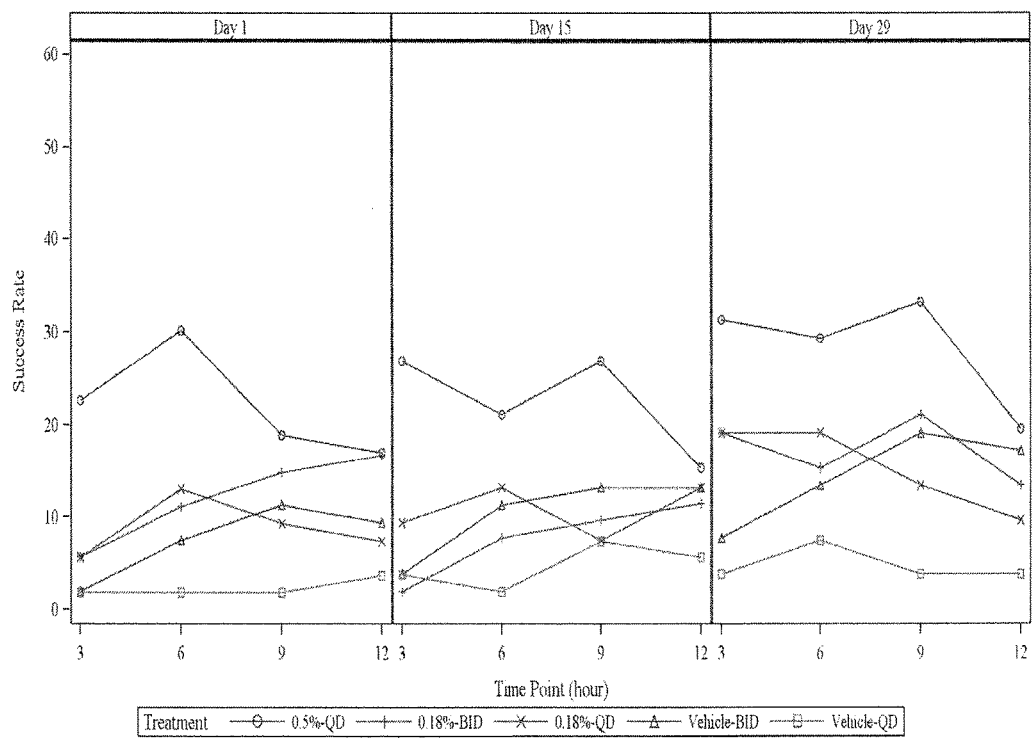
FIG. 1 illustrates composite success on Day 1, Day 15 and Day 29 after the initial treatment, using last observation carried forward (LOCF) approach in the intent to treat (ITT) population.

Various publications, articles and patents are cited or described in the background and throughout the specification, each of these references is herein incorporated by reference in its entirety. Discussion of documents, acts, materials, devices, articles or the like which have been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "erythema or a symptom associated therewith" is intended to encompass any type or classification of abnormal skin redness associated with or resulting from rosacea, e.g., erythema or a symptom associated therewith in a patient with rosacea. A major symptom of rosacea is erythema, which is a skin disorder that generally affects the cheeks, nose, chin, and forehead of a patient.

The term "erythema or a symptom associated therewith" encompasses different degrees or grades of erythema or a symptom associated therewith, from mild to severe.

For example, erythema or a symptom associated therewith can be rated by a clinician based on Clinician's Erythema Assessment Score (CEA) on a scale from 0 to 4, with 0 being clear skin with no signs of erythema; 1 being almost clear, slight redness; 2 being mild erythema, definite redness; 3 being moderate redness; and 4 being severe redness.

Erythema or a symptom associated therewith can also be rated by a patient based on Patient's Self Assessment (PSA, also called PSA-5 herein) on a scale from 0 to 4, with 0 being no redness; 1 being very mild redness; 2 being mild redness; 3 being moderate redness and 4 being severe redness.

In view of the present disclosure, a skin area that is affected by erythema or that is prone to be affected by erythema can be identified using any diagnostic signs or means known in the art, and can be treated by methods according to embodiments of the present invention.

The efficacy of the treatment can be measured using method known in the art. For example, the efficacy can be measured by the grades of improvement as evaluated by CEA, PSA or the combination of CEA and PSA, and the duration of the improvement.

As used herein, the term "brimonidine" refers to the compound (5-bromo-quinoxalin-6-yl)-(4,5-dihydro-1H-imidazol-2-yl)-amine having the structure of formula (I):

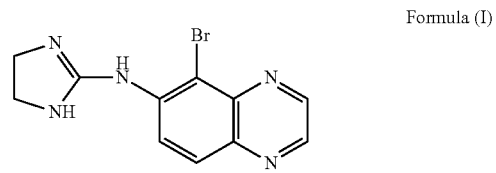 [SMILES: Brc1c(NC2=NCCN2)ccc2nccnc12]

Formula (I)

and any pharmaceutically acceptable salt of the compound, including, but not limited to, brimonidine tartrate.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

The term "topically administrable composition," a "topical composition," or a "topical formulation," as used herein, means any formulation or composition which is pharmaceutically and/or cosmetically acceptable for topical delivery of the specified compounds according to embodiments of the invention. Exemplary forms of formulation that can be used for topical administration in embodiments of the present invention include, but are not limited to, sprays, mists, aerosols, solutions, lotions, gels, creams, ointments, pastes, unguents, emulsions and suspensions.

The term "topically administrable composition" as used herein, also encompasses locally applied and locally acting formulations such as formulations for use with implants, injections, or patches.

The choice of topically administrable composition will depend on several factors, including, but not limited to, the nature of the symptoms to be treated or prevented, the physiochemical characteristics of the particular compound to be administered and of other excipients present, their stability in the formulation, the aesthetics of any given formulation, available manufacturing equipment, and cost constraints.

As used herein, the term "composition" is intended to encompass a product comprising the specified ingredient in the specified amount, as well as any product which results, directly or indirectly, from combinations of the specified ingredient in the specified amount.

As used herein, the term "subject" means any animal, preferably a mammal, most preferably a human, to whom will be or has been administered compounds or topical formulations according to embodiments of the invention. Preferably, a subject is in need of or has been the object of observation or experiment of, treatment or prevention of erythema or a symptom associated therewith.

As used herein, the term "instructions" when used in the context of a packaged product includes a publication, a recording, a diagram or any other medium of expression which can be used to communicate the usefulness of the packaged product for its designated use. The instructions can, for example, be affixed to or included within a container for the packaged product.

As used herein, the term "treatment" or "treating" refers to an amelioration, prophylaxis, or reversal of erythema or a symptom associated therewith, for example, by lessening or delaying the onset of the redness of the skin affected by the erythema or the symptom.

As used herein, a "safe and effective amount of brimonidine" means the amount of brimonidine that is effective to treat erythema or a symptom associated therewith, without causing unacceptable drug related adverse events, when administered to a subject.

As used herein, the phrase "unacceptable drug related adverse events," "unacceptable adverse drug events," and "unacceptable adverse drug reaction," shall all mean harm or undesired outcome associated with or caused by a proposed use of a drug, and the harm or undesired outcome reaches such a severity that a regulatory agency deems the drug unacceptable for the proposed use.

It has been discovered in the present invention that topical administration of a safe and effective amount of brimonidine, such as a topical composition comprising about 0.3% to about 10% by weight of brimonidine, to a skin area affected by erythema or a symptom associated therewith, provides effective treatment of erythema or a symptom associated therewith, without causing unacceptable drug related adverse events. For example, it was discovered that topical administration of a topical composition comprising increasing concentration of brimonidine to a skin area affected by erythema or a symptom associated therewith resulted in a clear dosage responsive increase in the efficacy and an increase in the systemic exposure. However, statistical analysis showed that the increase in systemic exposure ($C_{max}$) was not dose proportional, e.g., the increase in mean $C_{max}$ was much less than the increase in dose. It has also been discovered that, unlike the topical ophthalmic application, topical administration to an affected skin area a higher concentration of brimonidine resulted in increased efficacy without observable loss of efficacy over time. No unacceptable adverse event was observed with the treatment of higher concentration of brimonidine tested. Topical skin treatments of erythema or a symptom associated therewith with all concentrations and regimens tested resulted in significantly lower systemic exposure to brimonidine than the treatment with eye drops applied as recommended in the label of the ophthalmic products.

Such superior clinical activities of the higher concentrations of brimonidine, e.g., about 0.3% to about 10% by weight, have not been previously reported. The present discovery is surprising and unexpected, particularly in view of the previously reported efficacy and safety profiles of brimonidine in ophthalmic applications, where a significant loss of effectiveness over time was seen with the brimonidine 0.5% (w/w) formulation and the chronic use of much lower concentrations of brimonidine, e.g., 0.1% or 0.15% by weight, is preferred, because the lower concentrations provide improved tolerability while maintaining IOP-lowering efficacy.

Accordingly, in one general aspect, embodiments of the present invention relate to a method of providing a safe and effective treatment of erythema or a symptom associated therewith in a subject, comprising topically administering to a skin area affected by the erythema or the symptom a topical composition comprising about 0.3% to about 10% by weight brimonidine and a pharmaceutically acceptable carrier, wherein the topical administration effects a serum or plasma profile of brimonidine having a mean $C_{max}$ of about 54±28 pg/mL or less and a mean $AUC_{0-24hr}$ of about 568±277 pg·hr/mL or less. The mean $C_{max}$ and the mean $AUC_{0-24hr}$ correspond to the serum or plasma profile of brimonidine after ophthalmic treatment with 0.2% (w/w) brimonidine tartrate eye drops as recommended in the label of the ophthalmic product.

According to an embodiment of the present invention, upon topically administering the topical formulation to the affected skin area, the onset of noticeable effect, i.e., at least 1-grade improvement of the erythema or the symptom, is first observed. The noticeable effect is then progressed to maximum improvement, which includes 2-grade of improvement of the erythema or the symptom that lasts for a sustained period of time. The maximum improvement then declines to noticeable effect, which then disappears. The grades of improvement of the erythema or the symptom can be evaluated by Clinician's Erythema Assessment Score (CEA), a Patient's Self Assessment (PSA), or a combination of CEA and PSA.

According to an embodiment of the present invention, the topical administration of a topical composition comprising about 0.3% (w/w) to about 10% (w/w) brimonidine to a skin area affected by erythema or a symptom associated therewith results in significantly more effective treatment of the erythema and the symptom than a vehicle control for reduction of facial erythema associated with rosacea as measured by a 12 hour success profile evaluated on both CEA and PSA scales, without causing any unacceptable adverse effect.

In one embodiment, the 12 hour success profile comprises at least 1-grade improvement of the erythema or the symptom.

According to another embodiment of the present invention, the topical administration of a topical composition comprising about 0.3% (w/w) to about 10% (w/w) brimonidine to a skin area affected by erythema or a symptom associated therewith resulted in significantly more reduction of facial erythema associated with rosacea compared to a vehicle control as measured by a 12 hour success profile evaluated on both CEA and PSA scales, without causing any unacceptable adverse effect.

In an embodiment of the present invention, the 12 hour success profile comprises a noticeable effect of 1-grade improvement of the erythema or the symptom and about 1 hour to about 8 hours of a 2-grade improvement of the erythema or the symptom. According to embodiments of the present invention, the 2-grade improvement lasts, for example, at least about 6 hours, at least about 5 hours, at least about 4 hours, at least about 3 hours, at least about 2 hours or at least about 1 hour, depending on the applied dose, the particular subject, the severity and complications of erythema being treated, etc.

In a preferred embodiment, the 12 hour success profile comprises a noticeable effect of 1-grade improvement of the erythema or the symptom and about 2 hours to about 7 hours of a 2-grade improvement of the erythema or the symptom.

In another preferred embodiment, the 12 hour success profile comprises a noticeable effect of 1-grade improvement of the erythema or the symptom and about 3 hours to about 6 hours of a 2-grade improvement of the erythema or the symptom.

In yet another preferred embodiment, the 12 hour success profile comprises a noticeable effect of 1-grade improvement of the erythema or the symptom and about 2 hours to about 5 hours of a 2-grade improvement of the erythema or the symptom.

In a preferred embodiment, the erythema is erythema of rosacea.

In an embodiment of the present invention, the topically administrable composition comprises about 0.3%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or 10.0%, by weight of brimonidine, such as brimonidine tartrate.

In another embodiment of the present invention, the topically administrable composition comprises about 0.4%, about 0.45%, about 0.5%, about 0.55% or about 0.6%, by weight of brimonidine, such as brimonidine tartrate.

In a preferred embodiment, the topical composition comprises about 0.5% by weight of brimonidine, such as about 0.5% by weight of brimonidine tartrate.

To treat or prevent erythema or a symptom associated therewith, in view of the present disclosure, the topically administrable compositions of the invention can be topically applied directly to the affected area in any conventional manner known in the art, e.g., by dropper, applicator stick, or cotton swab, as a mist via an aerosol applicator, via an intradermal or transdermal patch, or by simply spreading a formulation of the invention onto the affected area with fingers, a sponge, a pad, or wipes. Generally, the amount of a topical formulation of the invention applied to the affected skin area ranges from about 0.0001 $g/cm^2$ of skin surface area to about 0.05 $g/cm^2$, preferably, 0.002 $g/cm^2$ to about 0.005 $g/cm^2$ of skin surface area. Typically, one to four applications per day are recommended during the term of treatment.

According to a preferred embodiment of the present invention, the topical composition is topically applied to the affected skin area once daily.

Methods of the present invention can be used in conjunction with one or more other treatments and medications for erythema or a symptom associated therewith, such as the medications used to treat the underlying disease that causes erythema, antihistamines to control itching, antibiotics, corticosteroids, intravenous immunoglobulins, acetaminophen, etc.

The other medicament or treatment can be administered to the subject simultaneously with, or in a sequence and within a time interval of, the administration of brimonidine, such that the active ingredients or agents can act together to treat or prevent erythema and symptoms associated therewith. For example, the other medicament or treatment and brimonidine can be administered in the same or separate formulations at the same or different times, i.e., before or after. Any suitable route of administration can be employed to deliver the additional treatment or medication.

Another aspect of the invention relates to a packaged product for providing a safe and effective treatment of erythema or a symptom associated therewith in a subject. The method comprises:

(1) obtaining a topical composition comprising about 0.3% to about 10% by weight brimonidine and a pharmaceutically acceptable carrier;

(2) devising instructions for topically administering the topical composition to a skin area affected by the erythema or the symptom to obtain the safe and effective treatment; and (3) providing the topical composition and the instructions in a unified package, wherein the topical administration effects a serum or plasma profile of brimonidine having a mean $C_{max}$ of about 54±28 pg/mL or less and a mean $AUC_{0-24hr}$ of about 568±277 pg·hr/mL or less.

In one embodiment of the invention, the topical composition is contained within one suitable container, such as a dropper, a jar, or a tube with a suitable small orifice size, such as an extended tip tube, made of any pharmaceutically suitable material. The topical formulations according to embodiments of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332. Optionally, an applicator can be provided in or attached to the container, or separately from the container.

In one embodiment of the invention, the instructions are, for example, a pamphlet or package label. The instructions explain how to administer topical formulations of the invention, in an amount and for a period of time sufficient to provide a safe and effective treatment of erythema or a symptom associated therewith. Preferably, the instructions include, for example, the dosage and administration instructions, the topical formulation's composition, the clinical pharmacology, drug resistance, pharmacokinetics, absorption, bioavailability, and contraindications.

Another aspect of the present invention relates to a topical gel composition for providing a safe and effective treatment of erythema or a symptom associated therewith in a subject. The topical gel composition comprises:

about 0.3% (w/w) to about 10.0% (w/w) brimonidine;

about 0.20% (w/w) to about 4.0% (w/w) gelling agent; and about 5.0% (w/w) to about 30.0% (w/w) at least one polyol, wherein the topical administration of the topical gel composition to a skin area affected by the erythema or the symptom effects a serum or plasma profile of brimonidine having a mean $C_{max}$ of about 54±28 pg/mL or less and a mean $AUC_{0-24hr}$ about 568±277 pg·hr/mL or less.

The topically administrable composition are prepared by mixing a pharmaceutically acceptable carrier with the safe and effective amount of brimonidine according to known methods in the art, for example, methods provided by standard reference texts such as, REMINGTON: THE SCIENCE AND PRACTICE OF PHARMACY 1577-1591, 1672-1673, 866-885(Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In a preferred embodiment, the topical gel composition comprises about 0.4% to about 0.6% by weight of brimonidine, more preferably, 0.5% by weight of brimonidine tartrate.

Suitable gelling agents known in the art, including those used in the two-phase or single-phase gel systems, can be used in the present invention. Some examples of suitable gelling agents are disclosed in REMINGTON: THE SCIENCE AND PRACTICE OF PHARMACY 1517-1518 (Alfonso R. Gennaro ed. 19th ed. 1995), which is hereby incorporated herein by reference. The gelling agents used in embodiments of the present invention, include, but are not limited to, one or more hydrophilic and hydroalcoholic gelling agents used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). The preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STABILEZE®" is between 0.5% to about 4%. Other preferred gelling agents include hydroxyethylcellulose, cellulose gum, MVE/MA decadiene crosspolymer, PVM/MA copolymer, glycerine polyacrylate, or a combination thereof.

Examples of carbomers that can be used in the present invention include, but are not limited to, Carbomer 910, 934P, 940, 941, 980 and 1342, and Carbopol® 974P and Carbopol® 980. Preferably, the carbomer is Carbomer 934P or Carbopol® 974P, and Carbopol® 980.

According to embodiments of the present invention, the amount of the carbomer in the composition is about 0.5%, 0.6%, 0.7%, 0.8%, 0.85%, 0.95%, 1.05%, 1.15%, 1.25%, 1.35%, 1.45%, 1.5%, 1.6%, 1.7%, 1.8%, 1.9% or 2.0% (w/w).

Polyol gel formulations with various ingredients solubilized therein have been used to minimize irritation when applied to the skin of a subject, while ensuring bioavailability of the active agent in the formulation. See Other III et al. "Gels and Jellies," pp. 1327-1344 of *Encyclopedia of Pharmaceutical Technology*, vol. 3 (ed. by Swarbrick, et al, pub. by Marcel Dekker, 2002); or Pena, "Gel Dosage Forms: Theory, Formulation, and Processing," pp. 381-388 of *Topical Drug Delivery Formulations*, (ed. by Osborne et al., pub. by Marcel Dekker, Inc., 1990). Polyols in gel formulations can serve one or more functions such as solubilizing agents, moisturizers, emollients, skin humectant, skin-penetration agents, etc. Suitable polyols that can be used in embodiments of the present invention include, but are not limited to, glycerine, propylene glycol, dipropylene glycol, hexylene glycol, butylene glycol, and liquid polyethylene glycols, such as polyethylene glycol 200 to 600.

According to embodiments of the present invention, the amount of the total polyols in the composition is about 5.0% to 30.0% (w/w), for example, about 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 17%, 20%, 25% or 30% (w/w).

Preferably, the topical gel composition comprises a first polyol and a second polyol, such as propylene glycol and glycerine, respectively.

According to embodiments of the present invention, the amount of each of the first and second polyols in the composition is independently about 4 to 15%, such as 4.5% to 6.5% (w/w), for example, 4.5%, 5.0%, 5.5%, 6.0% or 6.5% (w/w).

The pH of the topical formulations of the invention are preferably within a physiologically acceptable pH, e.g., within the range of about 4 to about 8, preferably, of about 6 to about 7.5, and more preferably about 4.5 to 6.5. To stabilize the pH, preferably, an effective amount of a buffer is included. In one embodiment, the buffering agent is present in the aqueous topical formulation in an amount of from about 0.05 to about 1 weight percent of the formulation.

The topical gel composition of the present invention can include one or more other ingredients, such as a protective agent, a cosmetic agent, an adsorbent, a preservative, an antioxidant, a surfactant, a skin-penetration agent, local anesthetics, analgesics etc.

In a preferred embodiment, a topical gel composition according to embodiments of the invention further comprises water dispersible form of titanium dioxide (TiO2), preferably at an amount that is sufficient to mask the color of brimonidine or another colored ingredient in the formulation, but would not cause irritation to the skin. TiO2 may cause mild irritation and reddening to the eyes, thus eye contact with the TiO2-containing topically administrable composition should be avoided. Titanium dioxide imparts a whiteness to the topically administrable composition and helps to increase the opacity and reduce the transparency of the composition. Titanium dioxide absorbs, reflects, or scatters light (including ultraviolet radiation in light), which can help protect products from deterioration. Titanium dioxide can also be used as a sunscreen to protect the user from the harmful effects of ultraviolet radiation that is part of sunlight.

According to embodiments of the present invention, the amount of water dispersible form of titanium dioxide in the composition is about 0.04 to 0.2%, such as 0.04%, 0.0425%, 0.0525%, 0.0625%, 0.0725%, 0.0825%, 0.09%, 0.10%, 0.15%, or 0.20% (w/w).

Suitable preservatives include, but are not limited to, quaternary ammonium compounds, such as benzalkonium chloride, benzethonium chloride, cetrimide, dequalinium chloride, and cetylpyridinium chloride; alcoholic agents, for example, chlorobutanol, phenylethyl alcohol, and benzyl alcohol; parabens such as methylparaben, ethylparaben, propylparaben, and butylparaben; antibacterial esters, for example, esters of parahydroxybenzoic acid; and other antimicrobial agents such as chlorhexidine, chlorocresol, benzoic acid, polymyxin, and phenoxyethanol. Preferably, the preservative is selected from the group consisting of sodium benzoate, phenoxyethanol, benzyl alcohol, methylparaben, imidazolidinyl urea and diazolidinyl urea.

In addition to brimonidine, the topically administrable composition according to embodiments of the invention can optionally include one or more other pharmaceutically active ingredients, including, but not limited to, medications used to treat the underlying disease that causes erythema, antihistamines to control itching, antibiotics, corticosteroids, intravenous immunoglobulins, acetaminophen, etc.

This invention will be better understood by reference to the non-limiting examples that follow, but those skilled in the art will readily appreciate that the examples are only illustrative of the invention as described more fully in the claims which follow thereafter.

EXAMPLE 1

Gel Topical Formulations

This example illustrates gel topical formulations that can be used in the present invention.

A first group of gel formulations is described in Table 1 below.

TABLE 1

| Ingredients | % (w/w) | % (w/w) | % (w/w) |
| --- | --- | --- | --- |
| Brimonidine tartrate | 0.3-0.6% | 0.6-3% | 3-10% |
| Methylparaben NF | 0.15% | 0.20% | 0.10% |
| Propylparaben NF | 0.03% | 0.02% | 0.04% |
| Hydroxyethylcellulose NF | 1.0% | 1.25% | 1.5% |
| Butylene glycol 1,3 | 3.0% | 6.0% | 18.0% |
| Glycerine | 2.0% | 4.0% | 12.0% |
| Disodium Edetate USP | 0.05% | 0.05% | 0.05% |
| Purified Water, USP | QS | QS | QS |
| TOTAL | 100% | 100% | 100% |

The pH of the formulation is adjusted to about 4.5 to 7.0.

A second group of gel formulations is described in Table 2 below.

TABLE 2

| Ingredients | % (w/w) | % (w/w) | % (w/w) |
| --- | --- | --- | --- |
| Brimonidine tartrate | 0.3-0.6% | 0.6-3.0% | 3.0-10% |
| Methylparaben | 0.20% | 0.20% | 0.20% |
| Propylparaben | 0.05% | 0.05% | 0.05% |
| KLUCEL ® | 2.0% | 2.5% | 1.0% |
| Propylene glycol | 3% | 6% | 15% |
| Glycerine, USP | 3% | 6% | 15% |
| 10% Titanium dioxide | 0.5% | 0.6% | 0.7% |
| Purified Water, USP | QS | QS | QS |
| TOTAL | 100% | 100% | 100% |

The ingredients are mixed together and aqueous sodium hydroxide is slowly added to the mixture until a pH of about 4.5 to 6.5 is reached and the gel is formed.

A third group of gel formulations is described in Table 3 below.

TABLE 3

| Ingredient | % (w/w) | % (w/w) | % (w/w) |
| --- | --- | --- | --- |
| Brimonidine tartrate | 0.3-0.6% | 0.6-3.0% | 3.0-10% |
| Carbomer 934P | 1.25% | 1.0% | 1.5% |
| Methylparaben | 0.2% | 0.15% | 0.20% |
| Phenoxyethanol | 0.4% | 0.35% | 0.4% |
| Glycerol | 5.5% | 10% | 15% |
| Kowet titanium dioxide | 0.0625% | 0.0725% | 0.0825% |
| Propylene glycol | 5.5% | 10% | 15% |
| DI Water | QS | QS | QS |
| TOTAL | 100% | 100% | 100% |

The ingredients are mixed together and aqueous sodium hydroxide is slowly added to the mixture until a pH of about 4.5 to 6.5 is reached and the gel is formed.

A fourth group of gel formulations is described in Table 4 below.

TABLE 4

| Ingredients | % (w/w) | % (w/w) | % (w/w) |
| --- | --- | --- | --- |
| Brimonidine tartrate | 0.3-0.6% | 0.6-3.0% | 3.0-10% |
| Methylparaben | 0.15% | 0.125% | 0.1% |
| Propylparaben | 0.05% | 0.05% | 0.06% |
| Carbopol ® 980 | 1.0% | 0.8% | 1.5% |
| Glycerin | 5.5% | 10% | 5% |
| 10% Titanium dioxide | 0.575% | 0.675% | 0.775% |
| Polyethylene glycol | 4.5% | 8% | 12% |
| Water | QS | QS | QS |
| TOTAL | 100% | 100% | 100% |

The ingredients are mixed together and stirred. Triethanolamine is added until a pH of about 5.5 to 7.0 is attained.

EXAMPLE 2

Comparative Bioavailability and Pharmacokinetics Study of Brimonidine Compositions This study was a randomized, evaluator-blinded, intra-individual comparative pharmacokinetic study of brimonidine tartrate, ophthalmic solution (0.2%) and topical gel (0.07%, 0.18% and 0.50%) applied under maximal use conditions for 29 days in subjects with moderate to severe erythema associated with rosacea. Major entrance criteria included clinical diagnosis of moderate to severe facial erythema associated with rosacea, CEA score ≥3and IOP level 11-21 mmHg. Intra-subject comparison of topical to ophthalmic exposure following one day treatment with brimonidine tartrate ophthalmic solution 0.2% was performed.

A total of 102 subjects were randomized: 24, 26, 25, and 27 subjects in 0.5% Gel QD, 0.18% Gel BID, 0.18% Gel QD, and 0.07% Gel BID, respectively. On the Day 1 visit, one drop of brimonidine tartrate ophthalmic solution 0.2% was administered to each eye every 8 hours over a 24 hour period. After a 2-day wash-out period, one gram of topical gel (0.07%, 0.18%, or 0.50% of brimonidine tartrate) was applied once (QD) or twice daily (BID) to the face of subjects for 4 weeks.

Blood samples for complete PK profiling were taken during the 24-hour ocular treatment (study Day 1) and during the first day of topical application (study Day 4), fifteen days of topical application (study Day 18) and after the last topical application up to 72 hours post-dose (study Day 32). Additional blood samples were collected before application (Day 10, Day 24). Brimonidine plasma concentrations were determined by using a validated LC-MS/MS method with a lower limit of quantification (LOQ) of 10 pg/mL.

The PK parameters for brimonidine were calculated using standard non-compartmental method and $C_{max}$, $AUC_{0-24hr}$ were analyzed statistically using log-transformed data. For both the differences between times administration routes and between treatment groups, the limits of the intervals were back-transformed into exponential to obtain 90% confidence intervals (90% CI) of the ratios of geometric means on the original scale. The statistical analysis was performed using all $C_{max}$ (BLQ values being replaced by the LOQ) and using only quantifiable $AUC_{0-24hr}$.

PK results demonstrated that:

(1) Ocular treatment: Administration of brimonidine tartrate 0.2% by ophthalmic route resulted in quantifiable exposure (>10 pg/mL) in all patients receiving TID treatment. The pharmacokinetic (PK) parameters of the ophthalmic solution have a mean $C_{max}$ of 54±28 pg/mL (range: 16-134 pg/mL) and a mean $AUC_{0-24hr}$ of 568±277 pg·hr/mL (range: 124-1490 pg·hr/mL). These were consistent with the known data of brimonidine tartrate 0.2% (w/w) ophthalmic solution, e.g., NDA:21-262, 0.2% Brimonidine Purite Multiple dose TID, $C_{max}$ 65±38 pg/mL.

(2) Topical treatments: Daily topical application of brimonidine Gel for 29 days resulted in quantifiable (>10 pg/mL) systemic exposure in 24%, 48%, 68% and 75% of subjects receiving brimonidine Gel 0.07% BID, 0.18% QD, 0.18% BID or 0.5% QD, respectively. At the end of the treatment period, the mean (±SD) $C_{max}$ were 13±9 pg/mL 17±20 pg/mL, 17±10 pg/mL, 25±24 pg/mL for brimonidine Gel 0.07% BID, 0.18% QD, 0.18% BID or 0.5% QD, respectively. Quantifiable $AUC_{0-24hr}$ were 172±87 pg·hr/mL, 183±113 pg·hr/mL, 267±119 pg·hr/mL, 364±216 pg·hr/mL for brimonidine Gel 0.07% BID, 0.18% QD, 0.18% BID or 0.5% QD, respectively.

The effect of multiple dose of brimonidine gel on PK profile (Time effect: Day 4/Day 18/Day 32) was assessed for each topical treatment groups. Systemic exposures of the first day of topical application were comparable to those observed after 29 days topical applications in all treatment groups, thus suggesting that there is no drug accumulation throughout the treatment duration (i.e. 4 weeks) whatever the dose and the dose regimen. Whatever the dose and dose regimen tested, the Topical/Ocular ratios calculated over the entire topical treatment period (Day 4, Day 18 and Day 32) was significantly lower than 1.

After topical application of brimonidine gel, systemic exposure increases with applied dose. However, statistical analysis showed that systemic exposure ($C_{max}$) is not dose proportional. The mean $C_{max}$ increased lower than dose proportionality.

The topical systemic exposure (expressed as $C_{max}$ or $AUC_{0-24hr}$) from the skin treatment was compared to the one obtained after ocular treatment. See Table 5.

In all the dosages and dose regimens tested the Topical/Ocular ratios calculated over the entire duration of the topical treatment period (Day 4, Day 18 and Day 32) were significantly lower than 1. The $C_{max}$ mean ratio was 0.2 for 0.07% BID group, ranged from 0.2 to 0.3 for 0.18% QD and BID groups and ranged from 0.3 to 0.6 for 0.5% QD group. For $C_{max}$, the upper limit of the 90% confidence interval did not include 0.8 whatever the dose and dose regimen tested. The highest ratio was observed in the 0.5% QD group (mean ratio 0.6, 90% CI [0.5-0.7]) after 15 days of application, but not confirmed at the end of the 29-day of topical treatment (mean ratio 0.4, 90% CI [0.3-0.4]). The same tendency was observed with the quantifiable $AUC_{0-24hr}$. The clinical study results demonstrated that the systemic exposure obtained after topical treatment with all concentrations and regimens tested in the study is significantly lower compared to the systemic exposure obtained with the eye drops applied as recommended in the label of the ophthalmic products.

In conclusion, quantifiable PK profiles (at least $C_{max}$) were observed in all treatment groups. It has been found that although systemic exposure increased with the applied dose of brimonidine, statistical analysis showed that the increase in systemic exposure ($C_{max}$) was not dose proportional, e.g., the increase in the mean $C_{max}$ was much less than the increase in the dose. No evidence for systemic accumulation was observed.

All evaluated concentrations and regimens were well tolerate and safe. No clinically meaningful reductions in mean IOP, vital signs or routine laboratory parameters were observed with any of the topical gel treatment groups. Increasing drug concentration or regimen had no effect on the incidence of related cardiac/vascular AEs. There is no identifiable relationship between any PK parameter and the incidence or severity of any AEs related to the topical gel. There were no SAEs reported during the treatment period with the topical gel for skin application (DAY 4 through study completion). Two SAEs were reported during the ophthalmic solution treatment period (DAYS 1-3) in two subjects, with one SAE (Acute Hypotensive Event) considered related to the ophthalmic solution. Both subjects with SAEs were discontinued from the study prior to any exposure to the topical gel.

The study results demonstrated that the systemic exposure obtained after topical treatment of the affected skin areas with all concentrations of brimonidine and regimens tested

TABLE 5 statistical comparison of the ocular and topical treatments

| Parameter | CD07805/47 Gel 0.5% QD Estimate (90% CI) | CD07805/47 Gel 0.18% BID Estimate (90% CI) | CD07805/47 Gel 0.18% QD Estimate (90% CI) | CD07805/47 Gel 0.07% BID Estimate (90% CI) |
|---|---|---|---|---|
| Cmax Ratio between Topical Administration Visit and Day 1 (Ophthalmic administration) | | | | |
| Day 4/Day 1 | 0.3 (0.3, 0.3) | 0.3 (0.2, 0.3) | 0.2 (0.2, 0.3) | 0.2 (0.2, 0.2) |
| Day 18/Day 1 | 0.6 (0.5, 0.7) | 0.3 (0.3, 0.4) | 0.2 (0.2, 0.3) | 0.2 (0.2, 0.2) |
| Day 32/Day 1 | 0.4 (0.3, 0.4) | 0.3 (0.3, 0.4) | 0.3 (0.2, 0.3) | 0.2 (0.2, 0.3) |
| Quantifiable $AUC_{0-24\ hr}$ Ratio between Topical Administration Visit and Day 1 (Ophthalmic administration) | | | | |
| Day 4/Day 1 | 0.6 (0.4, 0.7) | 0.4 (0.3, 0.5) | 0.3 (0.2, 0.4) | 0.1 (0.1, 0.3)[a] |
| Day 18/Day 1 | 0.7 (0.6, 0.9) | 0.5 (0.4, 0.6) | 0.3 (0.2, 0.4) | 0.5 (0.2, 0.8)[a] |
| Day 32/Day 1 | 0.5 (0.4, 0.7) | 0.5 (0.4, 0.6) | 0.3 (0.2, 0.4) | 0.4 (0.3, 0.7)[a] |

[a] should be taken with care due to the limited number of quantifiable $AUC_{0-24\ hr}$ (2 to 6)

N.B.: Day 4 → first topical administration; Day 18 → 15th topical administration; Day 32 → 29th and last topical administration is significantly lower compared to the systemic exposure obtained with the eye drops (0.2% by weight brimonidine tartrate) applied as recommended in the label of the ophthalmic products.

Based on results from this comparative bioavailability and pharmacokinetics study, concentrations of brimonidine higher than 0.2% (w/w) can be used for topical administration to an affected skin area for safe and effective treatment of a skin disorder.

EXAMPLE 3

Clinical Study on the Effectiveness and Safety of Brimonidine Tartrate Gel Compositions This was a 4-week treatment with 4-week follow-up, randomized, double-blind, parallel-group, vehicle-controlled, multicenter study investigating the efficacy and safety of a topical gel composition containing 0.5% brimonidine tartrate (Gel 0.5%) applied topically once daily (QD) and a topical gel composition containing 0.18% brimonidine tartrate (Gel 0.18%) applied topically once daily (QD) or twice daily (BID) compared to Vehicle Gel applied topically once daily (QD) or twice daily (BID), to affected skin areas of subjects with moderate to severe facial erythema associated with rosacea.

Major entrance criteria included clinical diagnosis of moderate to severe facial erythema associated with Rosacea, CEA score ≥3 and PSA-5 score ≥3, presence of no more than 2 facial lesions, and IOP level at least 10 mmHg.

Qualified subjects were randomized in a 1:1:1:1:1 ratio (block size of 5) to one of the five treatment arms (0.5% QD, 0.18% BID, 0.18% QD, Vehicle BID, Vehicle QD).

A total of 269 subjects from 17 clinical sites were randomized to Topical Gel or Vehicle Gel: 53, 54, 54, 53, and 55 subjects in the 0.5% QD, 0.18% BID, 0.18% QD, Vehicle BID, and Vehicle QD arms, respectively. All 269 subjects were included in the ITT and Safety population, and 237 subjects were included in the PP population.

CEA and PSA evaluation data were collected at each clinic visit at Hours 3, 6, 9, and 12 after study drug application. Data collected at 30 minutes after study drug application comprised the secondary endpoints of CEA Initial Effect and PSA Initial Effect. Subject-reported efficacy data were collected at clinic visits and on non-clinic days during the treatment period. Safety were assessed throughout the study.

The primary endpoint, Composite Success, is defined as a 2-grade improvement on both CEA and PSA-5 measured at Hours 3, 6, 9 and 12 on Day 29 after the treatment. Statistical analysis was performed to compare each active treatment (0.5% QD, 0.18% BID and QD) vs. the corresponding Vehicle QD or Vehicle BID, respectively. Additional analyses for Composite Success on early treatment visits Day 15 and Day 1 were performed to further investigate the early treatment effect.

Maximal drug effect peaked between approximately 3 to 6 hours after dosing. On Day 29, statistically significant difference between 0.5% QD vs. Vehicle QD was observed ($p<0.001$). Consistently, the same superiority of 0.5% QD vs. Vehicle QD was observed on Day 15 ($p<0.001$) and Day 1 ($p<0.001$). The statistical results based on the ITT population (LOCF approach) were confirmed in the population point (PP) population and three sensitivity analyses (i.e. imputing missing data by assigning failure, success, and average data, respectively).

As shown in FIG. 1, superior treatment effect was clearly demonstrated in 0.5% QD, followed by 0.18% BID and QD. Consistently, 0.5% QD showed strong and robust effect as measured by Composite Success throughout the 12 hour duration, starting on Day 1 and continued till Day 29. Therefore, no evidence of tachyphylaxis was observed. The magnitude of the treatment effects were general similar between 0.18% BID and 0.18% QD. The lower vehicle effect in the Vehicle QD regimen resulted in better statistical outcome for 0.18% QD vs. Vehicle QD comparison.

Figure 2:
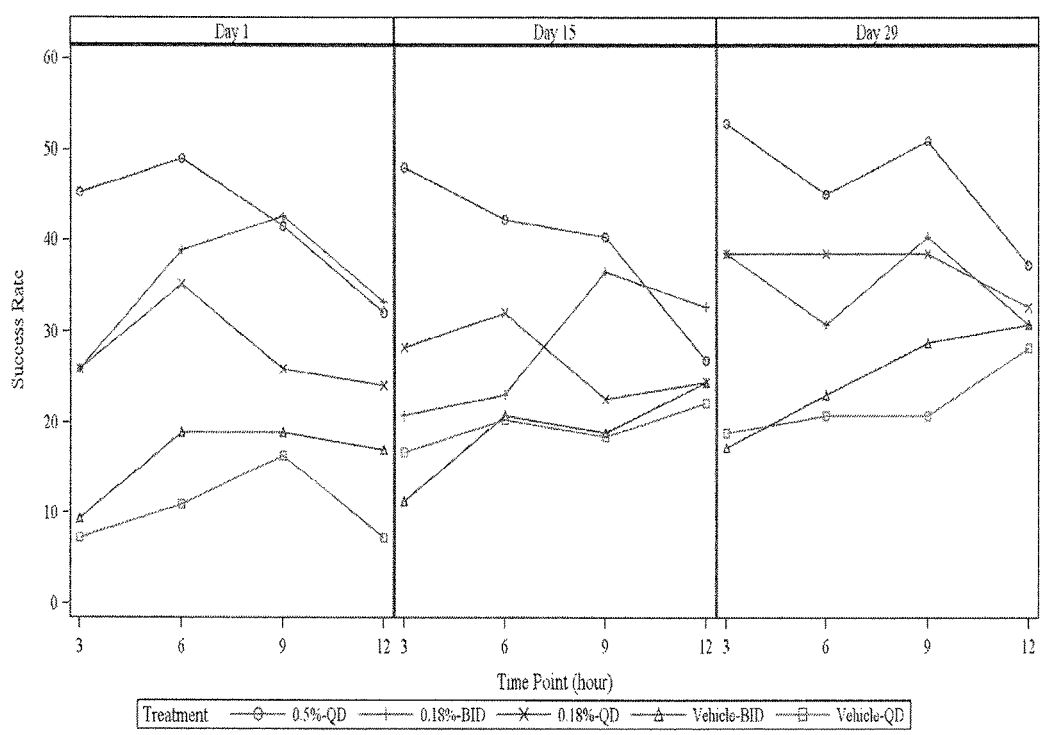
FIG. 2 illustrates CEA success on Day 1, Day 15 and Day 29 after the initial treatment, using LOCF approach in the ITT population.
Figure 3:
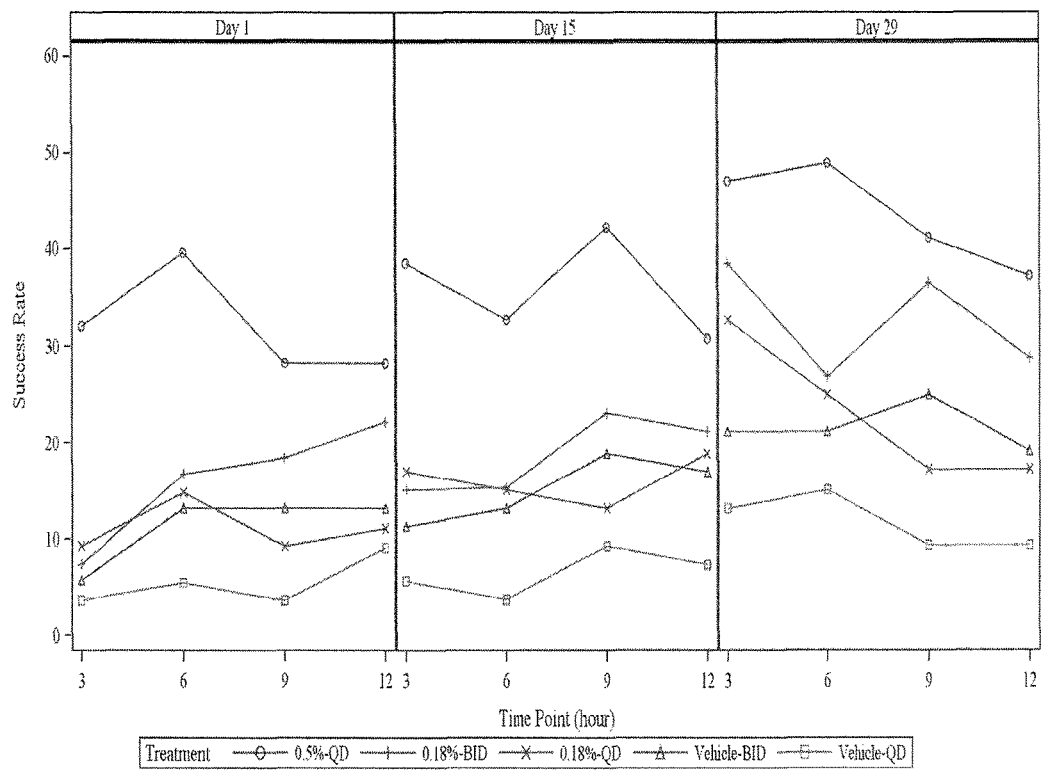
FIG. 3 illustrates PSA-5 success on Day 1, Day 15 and Day 29 after the initial treatment using LOCF approach in the ITT population.

In addition to the analysis on Composite Success, which is defined jointly by two independent static assessments, CEA-Success and PSA-5 Success were also analyzed individually. The magnitudes of the CEA-Success (FIG. 2) and PSA-5 (FIG. 3) Success were greater in all treatment groups compared to Composite Success but the pattern of the relative effects was same as observed in Composite Success. Consistently, 0.5% QD showed the greatest effect for CEA Success and PSA-5 Success; 0.18% QD and BID showed numerically better effect compared to Vehicle QD and BID, respectively.

The conclusion based on Composite Success, CEA-Success and PSA-5 Success was supported by PSA-5 Diary data (i.e. the subjects' daily recording of their facial redness) during the study.

The overall incidence of related adverse events (AEs) for the study was low. The number of related AEs was comparable between the treatment groups, and there was no significant difference in incidence of related adverse events between active and vehicle treatment arms. There was no significant increase in the number or severity of systemic or topical related AEs with increase in gel concentration or application frequency. No severe related AEs were reported during the study. There were no reported systemic cardiac AEs considered related to the study medication. No case of related facial flushing led to study discontinuation or interruption of daily treatment.

No clinically meaningful abnormal trends or shifts were observed in mean blood pressure (systolic and diastolic) or heart rate for any of the treatment groups during the treatment phase (Days 1, 15, and 29) or at the end of the follow-up period, and there was no observable difference in mean blood pressure or heart rate changes between active and vehicle arms. Increasing drug concentration or application frequency had no effect on the incidence of isolated vital sign abnormalities. There were no reported adverse events of acute hypotension, bradycardia, or syncope during the study. This clinical study demonstrated that Gel 0.5% QD possessed superior efficacy compared to the corresponding vehicle and Gel 0.18% QD and BID treatments evaluated in the study (primary endpoint: Composite Success defined as a 2-grade improvement on both CEA and PSA-5 at Hours 3, 6, 9, and 12 on Day 29). The primary outcome was supported by the secondary endpoints. No unacceptable drug related adverse event was observed. Safety and tolerability of Gel 0.5% QD is favorable. No evidence of tachyphylaxis or rebound was found in the study.

Unlike ophthalmic applications of brimonidine, where the chronic use of lower concentration of brimonidine, e.g., 0.1% (w/w), provides improved tolerability while maintaining IOP-lowering efficacy, the present clinical studies unexpectedly discovered that higher concentrations of brimonidine provide significantly improved clinical efficacy in treating erythema or related symptoms, while not causing any observable change in patient safety and tolerability as compared to lower concentrations of brimonidine.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of treating facial erythema associated with rosacea in a subject in need thereof, comprising once daily topically administering to a skin area of the subject affected by the facial erythema a topical composition comprising, relative to the total weight of the composition:
   0.5% by weight of brimonidine tartrate;
   about 8.0% to about 30.0% by weight in total of one or more polyols;
   about 0.20% to about 4.0% by weight of a gelling agent; and
   a pharmaceutically acceptable carrier,
   wherein the topical administration results in more reduction of the facial erythema compared to a vehicle control as measured by a 12 hour success profile evaluated on both Clinician's Erythema Assessment scores and Patient's Self Assessment scales without causing unacceptable drug related adverse events, and the 12 hour success profile comprises at least a 1-grade improvement of the facial erythema.

2. The method of claim 1, wherein the 12 hour success profile further comprises about 1 hour to about 8 hours of a 2-grade improvement of the facial erythema.

3. The method of claim 1, wherein the 12 hour success profile further comprises about 3 hours to about 6 hours of a 2-grade improvement of the facial erythema.

4. The method of claim 1, wherein the gelling agent comprises a carbomer, and the topical composition comprises about 0.5% to about 2.0% by weight of the carbomer relative to the total weight of the composition.

5. The method of claim 4, wherein the carbomer is selected from the group consisting of carbomer 934P, carbomer 974P, and carbomer 980.

6. The method of claim 5, wherein the topical composition comprises a first polyol and a second polyol, and the amount of each of the first and second polyols in the composition is independently about 4 to 15% by weight relative to the total weight of the composition.

7. A method of treating facial erythema associated with rosacea in a subject in need thereof, comprising once daily topically administering to a skin area of the subject affected by the facial erythema a topical composition comprising, relative to the total weight of the composition:
   0.5% by weight of brimonidine tartarate;
   about 5.0% to about 30.0% by weight of at least one polyol;
   about 0.5% to about 2.0% by weight of a gelling agent; and
   a pharmaceutically acceptable carrier,
   wherein the gelling agent comprises a carbomer selected from the group consisting of carbomer 934P, carbomer 974P, and carbomer 980, and
   wherein the topical administration results in more reduction of the facial erythema compared to a vehicle control as measured by a 12 hour success profile evaluated on both Clinician's Erythema Assessment scores and Patient's Self Assessment scales without causing unacceptable drug related adverse events, and the 12 hour success profile comprises at least a 1-grade improvement of the facial erythema and about 1 hour to about 8 hours or about 3 hours to about 6 hours of a 2-grade improvement of the facial erythema.

8. The method of claim 7, wherein the topical composition further comprises a preservative selected from the group consisting of sodium benzoate, phenoxyethanol, benzyl alcohol, methylparaben, imidazolidinyl urea and diazolidinyl urea.

* * * * *